United States Patent

Suzuki et al.

[11] Patent Number: 5,420,351
[45] Date of Patent: May 30, 1995

[54] AROMATIC DIAMINE COMPOUNDS

[75] Inventors: Osamu Suzuki; Hirohiko Yokomizo; Takeshi Arai; Namiko Nakajima, all of Tokyo, Japan

[73] Assignee: Nisshinbo Industries, Inc., Tokyo, Japan

[21] Appl. No.: 336,073

[22] Filed: Nov. 7, 1994

[30] Foreign Application Priority Data

Nov. 25, 1993 [JP] Japan .................. 5-320988

[51] Int. Cl.⁶ .......................................... C07C 211/54
[52] U.S. Cl. .................................................. 564/308
[58] Field of Search ......................................... 564/308

[56] References Cited

U.S. PATENT DOCUMENTS

| | | | |
|---|---|---|---|
| 3,532,748 | 10/1970 | Smith | 504/459 |
| 4,539,507 | 9/1985 | VanSlyke et al. | 313/504 |
| 5,298,661 | 3/1994 | Shimada et al. | 564/434 |

OTHER PUBLICATIONS

Appl. Phys. Lett., 51 (12), 913 (1987).

*Primary Examiner*—Richard L. Raymond
*Attorney, Agent, or Firm*—Adduci, Mastriani, Schaumberg & Schill

[57] ABSTRACT

An aromatic diamine compound represented by formula (1):

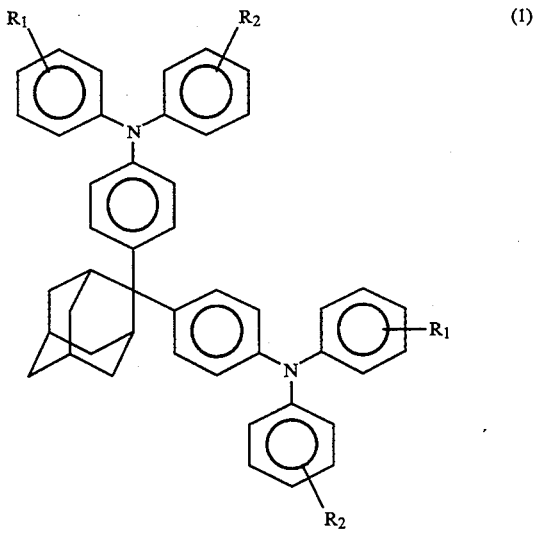

wherein $R_1$ and $R_2$, which may be the same or different, are each a hydrogen atom or a lower alkyl group; and an aromatic diamine compound useful as an intermediate for the synthesis of the above compound (1), represented by formula (2):

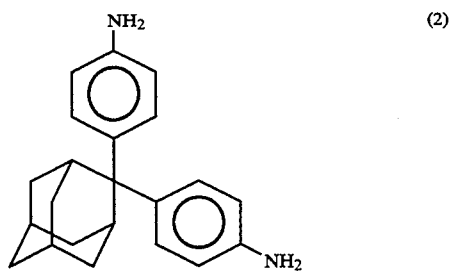

The compound (1) alleviates the problems of the prior art, and is unlikely to cause crystallization by heat and has a melting point and a glass transition temperature both higher than those of conventional compounds.

2 Claims, 4 Drawing Sheets

AROMATIC DIAMINE COMPOUNDS

BACKGROUND OF THE INVENTION

1. Field of the Invention

The present invention relates to aromatic diamine compounds. More particularly, the present invention relates to an aromatic diamine compound which can be used as a hole transport material for organic EL (electroluminescence) device, a hole transport material for an organic thin film photocell, a carrier transport material for electrophotography, etc.; as well as to an aromatic diamine compound which is useful as a precursor for the synthesis of the above aromatic diamine compound.

2. Prior Art

As the aromatic diamine compounds used for the above applications, there can be cited, for example, 1,1-bis(4-di-p-tolylaminophenyl)cyclohexane represented by the following formula (3), used as a hole transport material for organic EL device [U.S. Pat. No. 4,539,507]

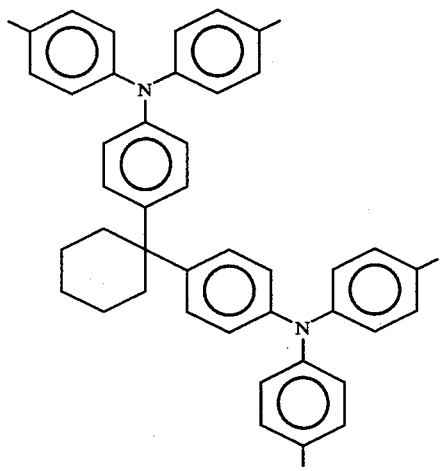

(3)

and N,N'-diphenyl-N,N'-bis(m-tolyl)benzidine represented by the following formula (4), used as a hole transport material for organic EL device [Appl. Phys. Lett., 51(12), 913 (1987)].

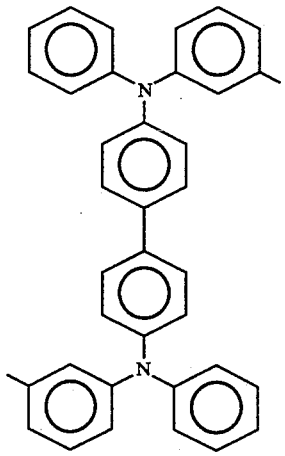

(4)

The compounds represented by the above formulas (3) and (4), however, have low melting points [174° C. in the case of the compound (3) and 165° C. in the case of the compound (4)]and low glass transition temperatures [77.7° C. in the case of the compound (3) and 66.5° C. in the case of the compound (4)]; as a result, when they are used in an organic EL device and the EL device is operated, they cause crystallization by the heat generated during the operation and the hole transport layer is deformed and an emission reduced. Thus, it has been required to develop a new material which has a high melting point and a high glass transition temperature and which is unlikely to cause crystallization.

OBJECT AND SUMMARY OF THE INVENTION

The object of the present invention is to provide an aromatic diamine compound which is free from the problems of the prior art and which is unlikely to cause crystallization by heat and has a melting point and a glass transition temperature both higher than those of conventional compounds, and an aromatic diamine compound which is useful as a precursor for the synthesis of the above aromatic diamine compound.

The requirements for a compound having a high melting point and a high glass transition temperature are, for example:

(1) a high molecular weight, (2) high molecular symmetry, and (3) good planeness of a molecule.

The requirements for a compound having an improved amorphous state preservation and resistance to crystallization are:

(1) low molecular symmetry, (2) bulky substituent(s), and (3) no planeness a molecule.

The contradictory requirements mentioned above must be solved in order to achieve the above object of the present invention and, accordingly, considerable design of compounds is necessary. The present inventors made an extensive study and discovered that the compound represented by the following formula (1) [hereinafter referred to as compound (1), in some cases] is unlikely to cause crystallization by heat and moreover has a higher melting point and glass transition temperature than those of conventional compounds. The finding has led to the completion of the present invention.

According to the present invention, there is provided an aromatic diamine compound represented by formula (1):

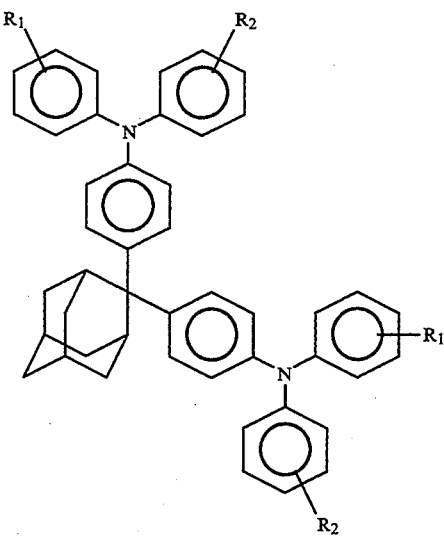

wherein $R_1$ and $R_2$, which may be the same or different, are each a hydrogen atom or a lower alkyl group.

According to the present invention, there is also provided an aromatic diamine compound represented by formula (2):

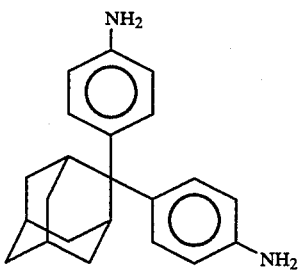

BRIEF DESCRIPTION OF THE DRAWINGS

In FIG. 4, 1 is a transparent electrode; 2 is a transport layer; 3 is an emitting layer; and 4 is an aluminum electrode.

DETAILED DESCRIPTION OF THE INVENTION

Figure 1:
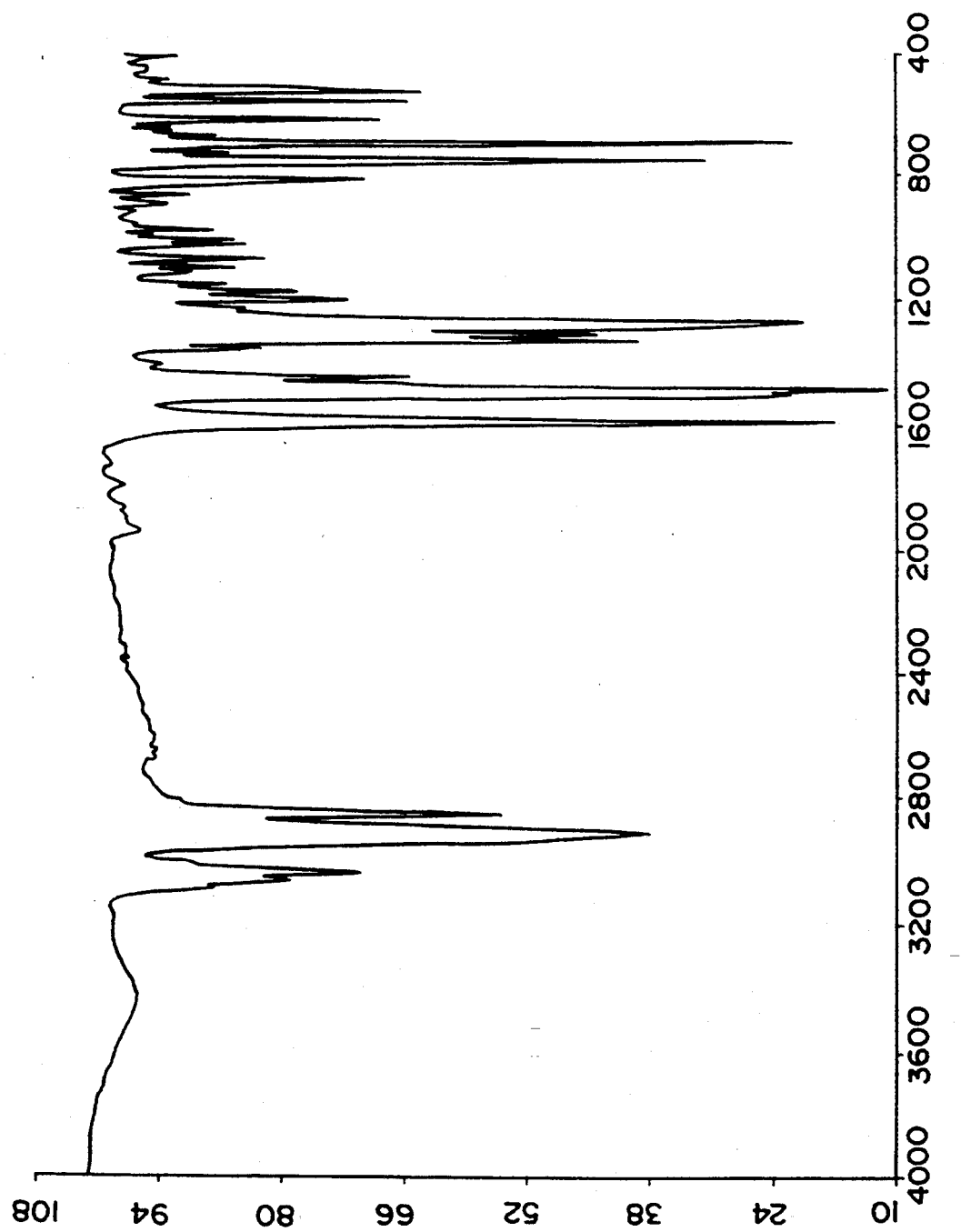
FIG. 1 is the IR spectrum of a compound of the present invention obtained in Example 2.

The present invention is hereinafter described in detail.

The aromatic diamine compound of the present invention is represented by the above formula (1), as mentioned above. In the formula (1), $R_1$ and $R_2$ may be the same or different and each are a hydrogen atom or a lower alkyl group such as methyl, ethyl, propyl or pentyl.

As is appreciated from the formula (1), the present compound is a compound in which the cyclohexylidene group of the known compound (3) is converted into an adamantylidene group.

The present compound represented by the formula (1) can be produced, for example, by the following process using the precursor of the present invention, represented by the formula (2).

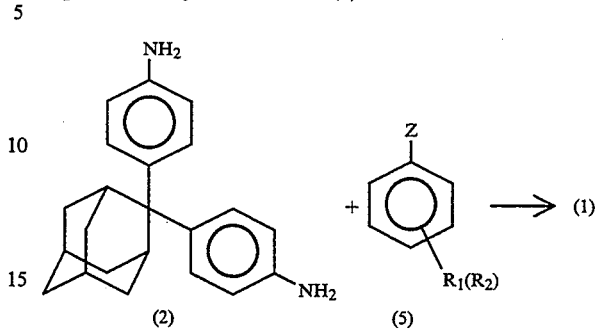

That is, the precursor (2) of the present invention is reacted with an excess of halogenated aromatic compound (5) in the presence of a copper powder (or a copper oxide or a copper halide) and a base at about 150°–250° C.

As the halogenated aromatic compound, there can be used iodobenzene, chloroiodobenzene, fluoroiodobenzene, iodotoluene, fluoroiodotoluene, iodoanisole, dichloroiodobenzene, difluoroiodobenzene, dimethyliodobenzene, ethyliodobenzene, 3,5-bis(trifluoromethyl iodobenzene, n-buytliodobenzene, tert-butyliodobenzene, iodonaphthalene, trichloroiodobenzene, tetrachloroiodobenzene, tetramethyliodobenzene, pentamethyliodobenzene, etc.

As the base, there can be used sodium hydroxide, potassium hydroxide, potassium carbonate, etc.. The reaction shown in the above reaction formula is conducted generally in the absence of any solvent, but there may be used a solvent such as saturated hydrocarbon which has high boiling temperature (e.g. dodecane or tridecane), aromatic hydrocarbon (e.g. nitrobenzene, dichlorobenzene, trimethylbenzene or hexamethylbenzene) or the like.

In the above reaction, the halogenated aromatic compound (5) is used in an amount of, for example, 5 moles or more per mole of the precursor (2); and the copper powder and the base are used in amounts of, for example, 1-2 moles and 1-1.2 moles, respectively, per mole of the halogenated aromatic compound (5). The reaction temperature is, for example, the boiling point of the halogenated aromatic compound (5), and the reaction time is, for example, 3-8 hours.

The precursor of the present invention, represented by the formula (2) can be prepared, for example, by the following process.

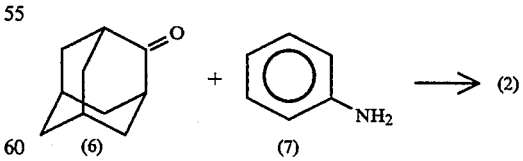

That is, adamantanone (6) is reacted with aniline (7) in the presence of hydrogen chloride, with stirring.

In the above reaction, aniline may be replaced by an aniline derivative in which the p-position relative to the amino group has no substituent. As such an aniline derivative, there can be cited, for example, aminobenzonitrile, aminoisophthalonitrile, aminobenzotrifluoride, aminochlorobenzotrifluoride, aminofluorobenzotrifluoride, amino-N,N-dimethylaniline, 3,5-bis(trifluoromethyl)aniline, chloromethylaniline, dichloroaniline, difluoroaniline, dimethoxyaniline, dimethylaniline, ethylaniline, anisidine and sec-butylaniline, etc..

In the above reaction, aniline (7) is used in an amount of, for example, 2.1 moles or more per mole of adamantanone (6); hydrogen chloride is used in an amount of, for example, 2 moles or more per mole of aniline (7). The reaction is conducted in the absence of any solvent or in a lower alcohol. The reaction temperature is, for example, about 120° C. and the reaction time is, for example, 100–150 hours.

The aromatic diamine compound (1) of the present invention can be used as a hole transport material for an organic EL device, a hole transport material for an organic thin film photovoltaic cell, a carrier transport material for an electrophotograph, etc. When the compound is used, for example, as a hole transport material for an organic EL device, the compound is vapor-deposited on a transparent anode of, for example, indium-tin oxide; also, aluminum-quinolinol complex is vapor-deposited as an emitting layer; further, a magnesium alloy is vapor-deposited as a cathode.

The present compound (1) is a compound in which the cyclohexylidene group of the known compound (3) is converted into an adamantylidene group. Therefore, the compound (1) has a molecular weight which is larger by 52 than known compound (3); more bulky; has reduced planeness of a molecule; has a high melting point and a high glass transition temperature; is unlikely to cause crystallization by heat; and has good thin-film formability. When used in, for example, an organic EL device, the compound (1) becomes an excellent hole transport material.

The present invention is hereinafter described in more detail by way of Examples.

EXAMPLE 1

Synthesis of 2,2-di-4-aminophenyladamantane (compound No. 2-1)

To a mixture of 10.0 g of 2-adamantane and 12.5 g of aniline, 11.7 ml of concentrated hydrochloric acid was added with ice-cooling. The mixture was stirred at 120° C. for 6 days. Then the reaction mixture was suspended in 1N hydrochloric acid. The suspension was washed with chloroform. The aqueous layer was made alkaline with an aqueous sodium hydroxide solution and then extracted with chloroform. The chloroform layer was washed with water, dried and subjected to distillation to remove chloroform and aniline, whereby a crude product was obtained. The crude product was purified by silica gel column chromatography and recrystallized from ethanol to obtain 12.8 g (yield: 60%) of an intended compound mentioned above.

Melting point: 249.5°–252.6° C. NMR (CDCl$_3$,δ): 1.8 ppm, bs, 8H 2.1 ppm, bs, 4H 3.1 ppm, bs, 2H 3.4 ppm, bs, 4H 6.85 ppm, dd, 16H IR (KBr, cm$^{-1}$): 3369, 3348, 1629, 1615, 1283, 814,

EXAMPLE 2

Synthesis of 2,2-bis(4-diphenylaminophenyl)-adamantane (compound No. 1-1)

A mixture of 2.0 g of 2,2-di-4-aminophenyladamantane, 33.8 g of iodobenzene, 2.5 g of a copper powder and 3.5 g of potassium carbonate were stirred in a nitrogen atmosphere at 183°–184° C. for 5 hours to obtain 5.0 g of a crude product. The crude product was purified by silica gel column chromatography to obtain 3.57 g (yield: 91%) of an intended compound mentioned above, as a white powder. It was further purified by sublimation.

Melting point: decomposed at 300° C. Glass transition temperature: 119.9° C. Crystallization temperature by DSC: no crystallization was seen.

NMR (CDCl$_3$,δ): 1.7 ppm, bs, 6H 1.8 ppm, bs, 6H 2.1 ppm, bs, 4H 3.1 ppm, bs, 2H 6.9–7.2 ppm, m, 24H IR (KBr): shown in FIG. 1 UV (CDCl$_3$)λ$_{max}$: 308.5

EXAMPLE 3

Synthesis of 2,2-bis(4-di-m-tolylaminophenyl)adamantane (compound No. 1-2)

A mixture of 2.0 g of 2,2-di-4-aminophenyladamantane, 36.1 g of m-iodotoluene, 2.5 g of a copper powder and 3.5 g of potassium carbonate were stirred in a nitrogen atmosphere at 183°–184° C. for 5 hours to obtain 5.7 g of a crude product. The crude product was purified by silica gel column chromatography to obtain 3.98 g (yield: 93%) of an intended compound mentioned above, as a white powder.

Melting point: 219.4° C. Glass transition temperature: 95.4° C. Crystallization temperature by DSC: 172.8° C.

Figure 2:
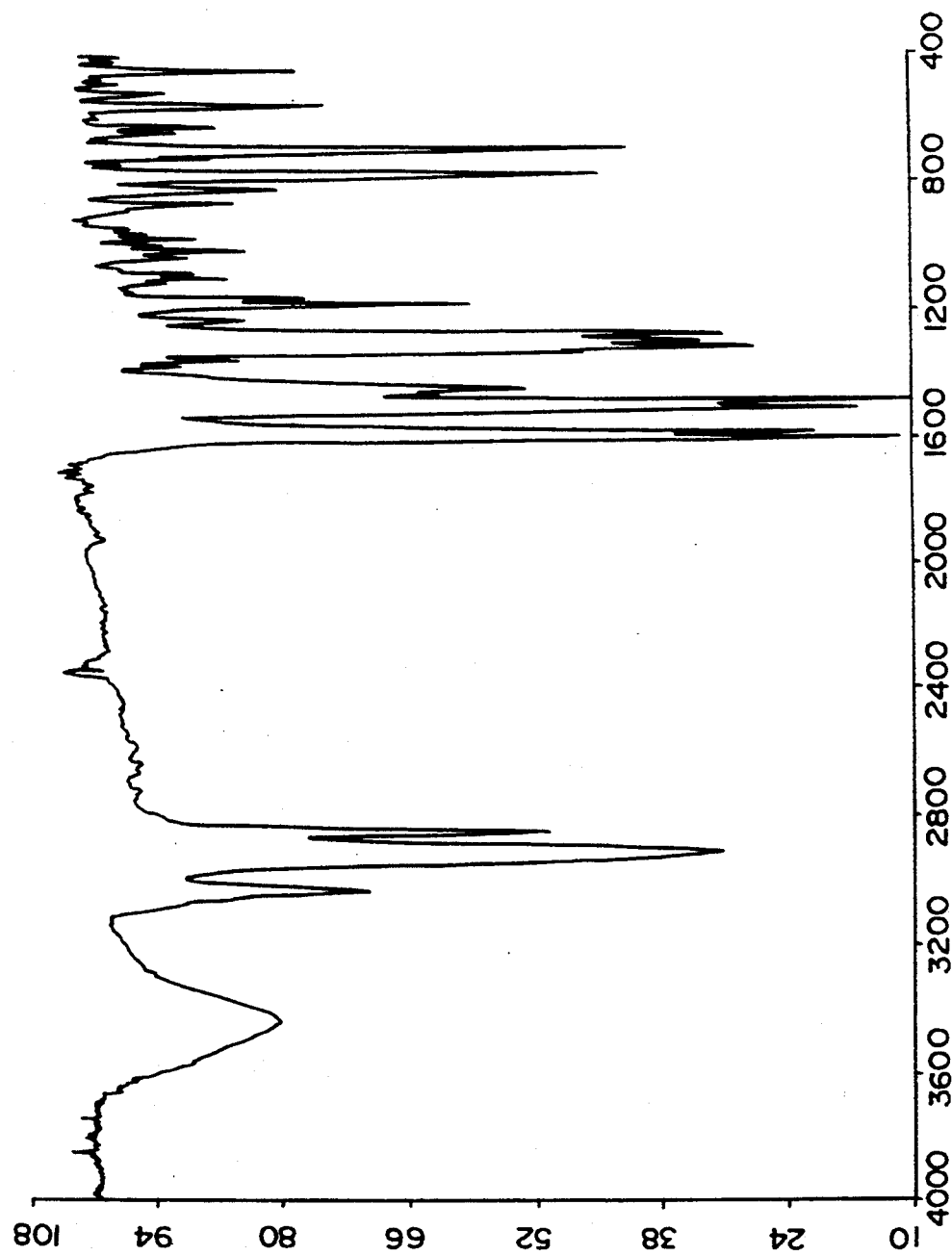
FIG. 2 is the IR spectrum of a compound of the present invention obtained in Example 3.

NMR (CDCl$_3$,δ): 1.7 ppm, bs, 6H 1.8 ppm, bs, 6H 2.1 ppm, bs, 4H 2.24 ppm, s, 12H 3.1 ppm, bs, 2H 6.8–7.2 ppm, m, 24H IR (KBr): shown in FIG. 2 UV (CHCl$_3$)λ$_{max}$: 369.4

EXAMPLE 4

Synthesis of 2,2-bis(4-di-p-tolylaminophenyl)adamantane (compound No. 1-3)

A mixture of 2.0 g of 2,2-di-4-aminophenyladamantane, 36.1 g of p-iodotoluene, 2.5 g of a copper powder and 3.5 g of potassium carbonate were stirred in a nitrogen atmosphere at 183°–184° C. for 5 hours to obtain 5.1 g of a crude product. The crude product was purified by silica gel column chromatography to obtain 3.81 g (yield: 89%) of an intended compound mentioned above, as a white powder.

Melting point: 253.4° C. Glass transition temperature: 114.5° C. Crystallization temperature by DSC: 149.7° C.

Figure 3:
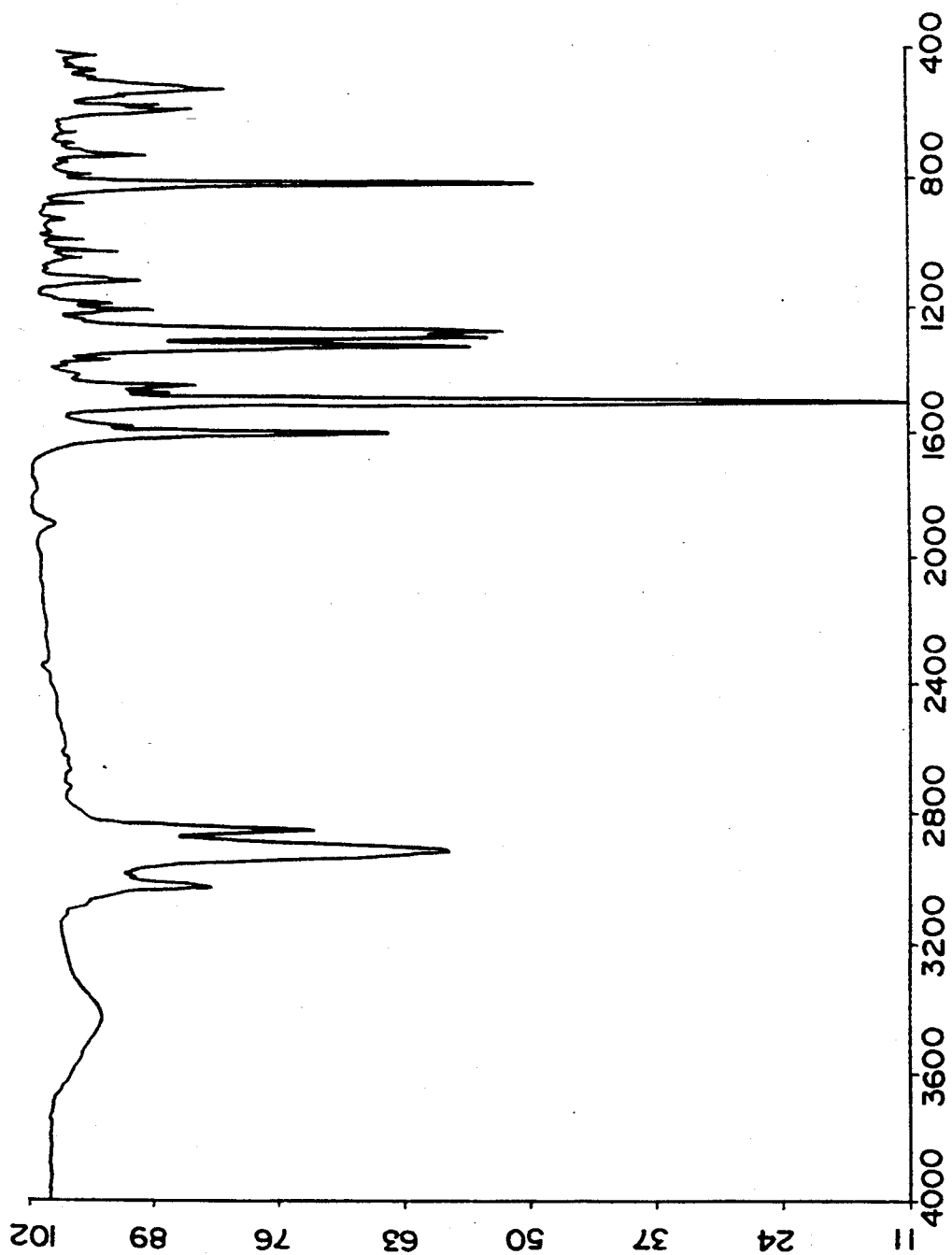
FIG. 3 is the IR spectrum of a compound of the present invention obtained in Example 4.

NMR (CDCl$_3$,δ): 1.7 ppm, bs, 2H 1.8 ppm, bs, 2H 2.1 ppm, bs, 4H 2.24 ppm, s, 12H 3.1 ppm, bs, 2H 6.8–7.2 ppm, m, 24H IR (KBr): shown in FIG. 3 UV (CHCl$_3$) λ$_{max}$: 379.6

Reference Example (Production of EL device)

Figure 4:
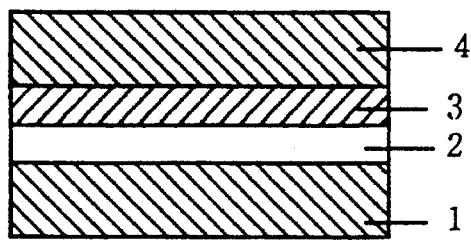
FIG. 4 is the sectional view of an organic EL device using a compound of the present invention.

As shown in FIG. 4, a glass substrate (25 mm×25 mm×1.0 mm) to which an indium-tin oxide (hereinafter referred to as ITO) film of 100 nm in thickness was adhered, was used as a transparent electrode 1. This transparent substrate was subjected to ultrasonic cleaning with pure water for 10 minutes and then with ethanol for 10 minutes, then dried, and fixed to the substrate holder of a vacuum deposition apparatus. 5 mg of 2,2-bis(4-diphenylaminophenyl) adamantane (compound No. 1—1) was placed in a boat made of tungsten. 10 mg of aluminum-quinolinol complex (hereinafter referred to as Alq$_3$)was placed in another boat made of tungsten. The two boats were fitted to the vacuum deposition apparatus. 23 mg of aluminum was placed in a crucible, and the crucible was fitted to the vacuum deposition apparatus. The pressure of the inside of the bell jar was reduced to $1.5\times10_{-5}$ Torr. Then, the boat containing the compound No. 1-1 was heated to deposit the compound No. 1-1 on the transparent substrate to form a hole transport material 2 of 500 nm in thickness. Further, the boat containing Alq3 was heated to deposit Alq3 on the transport layer 2 to form an emitting layer 3 of 500 nm in thickness. Finally, the crucible containing aluminum was heated to deposit aluminum on the emitting layer 3 to form an aluminum electrode 4 of 1,000 Å in thickness, whereby an EL device was produced.

A direct current was applied to the EL device with the ITO electrode and the aluminum electrode used as an anode and a cathode, respectively. Green emission of 2,000 cd/m² was obtained when the operating voltage was 10 V. The EL device had good durability.

What is claimed is:

1. An aromatic diamine compound represented by formula (1)

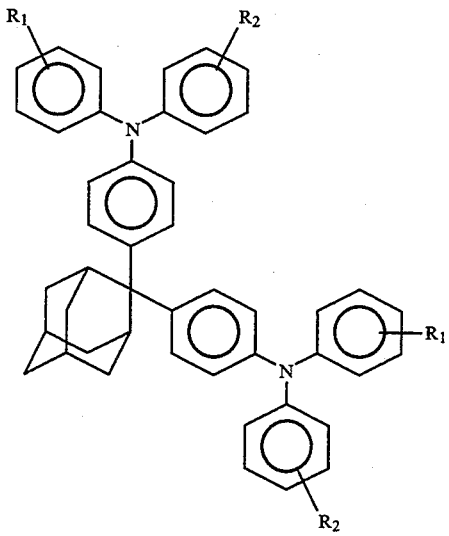

wherein $R_1$ and $R_2$, which may be the same or different, are each a hydrogen atom or a lower alkyl group.

2. An aromatic diamine compound represented by formula (2):

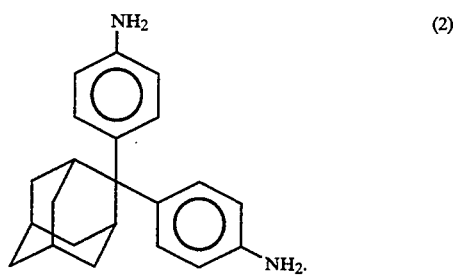

* * * * *